(12) United States Patent
Groome et al.

(10) Patent No.: US 6,620,590 B2
(45) Date of Patent: Sep. 16, 2003

(54) DIAGNOSIS OF PRE-ECLAMPSIA

(75) Inventors: Nigel Patrick Groome, Oxford (GB); Philip Gerald Knight, Reading (GB); William Leigh Ledger, Sheffield (GB); Christopher Willard George Redman, Oxford (GB); Shanthi Muttukrishna, Oxford (GB)

(73) Assignees: Isis Innovation Limited, Oxford (GB); The University of Reading, Reading (GB); Oxford Brookes University, Oxford (GB)

( * ) Notice: Subject to any disclaimer, the term of this patent is extended or adjusted under 35 U.S.C. 154(b) by 0 days.

(21) Appl. No.: 09/840,992

(22) Filed: Apr. 25, 2001

(65) Prior Publication Data

US 2001/0055781 A1 Dec. 27, 2001

Related U.S. Application Data

(63) Continuation of application No. 09/214,599, filed as application No. PCT/GB97/01880 on Jul. 11, 1997, now abandoned.

(30) Foreign Application Priority Data

Jul. 11, 1996 (GB) .............................................. 9614615

(51) Int. Cl.$^7$ ...................... G01N 33/53; G01N 33/543; C07K 16/00
(52) U.S. Cl. ...................... 435/7.1; 435/7.94; 435/7.92; 435/70; 435/240.2; 436/63; 436/65; 436/86; 436/87; 436/501; 436/503; 436/504; 436/510; 436/518; 530/351; 530/388.24; 530/399; 424/85.1; 424/85.2; 424/139.1; 424/141.1; 514/28; 514/177; 514/548; 514/565; 514/899
(58) Field of Search ................................ 435/70, 240.2, 435/7.1, 7.92, 7.94; 436/86, 65, 87, 503, 504, 510, 63, 501, 518; 424/85.1, 85.2, 139.1, 141.1; 530/351, 399, 388.24; 514/177, 548, 565, 899, 2.8

(56) References Cited

U.S. PATENT DOCUMENTS

| | | | |
|---|---|---|---|
| 5,198,366 A | 3/1993 | Silberman | .................... 436/86 |
| 5,543,138 A | 8/1996 | Keith | .................... 424/85.1 |
| 5,545,616 A | 8/1996 | Woodruff | ................... 514/8 |
| 5,580,554 A | 12/1996 | Keith | .................... 424/85.1 |
| 5,811,416 A | 9/1998 | Chwalisz et al. | ........... 514/177 |

FOREIGN PATENT DOCUMENTS

| | | |
|---|---|---|
| EP | 0 359 274 | 3/1990 |
| EP | 0 701 131 | 3/1996 |
| WO | 87/05702 | 9/1987 |

OTHER PUBLICATIONS

Wallace et al. Prenatal Diagnosis, vol. 15, 1995, pp. 359–362.*

McConnel et al., Clinical Chemistry, 42(8), pp. 1159–1167 (1996).

Muttukrishna et al., Clinical Endocrinology, 42, pp. 391–397 (1995).

Lindheimer et al., The Lancet, 349, pp. 1266–1267 (1997).

Mittukrishna et al., The Lancet, 349, pp. 1285–1288 (1997).

Mizunuma et al., Inhibin, Activin Follistatin, (Proc. Int. Symp.), 3, pp. 151–161 (1997).

Petraglia et al., Frontiers in Neuroendocrinology, 11/1, pp. 6–37 (1990).

* cited by examiner

*Primary Examiner*—Christopher V. Chin
*Assistant Examiner*—Lisa J. Cook
(74) *Attorney, Agent, or Firm*—Wenderoth, Lind & Ponack, L.L.P.

(57) ABSTRACT

A method for diagnosis of pre-eclampsia is disclosed, which comprises measuring the hormone inhibin A in a biological sample such as maternal serum. The method allows non-invasive, early diagnosis and can be used to predict the onset of secondary symptoms.

4 Claims, 4 Drawing Sheets

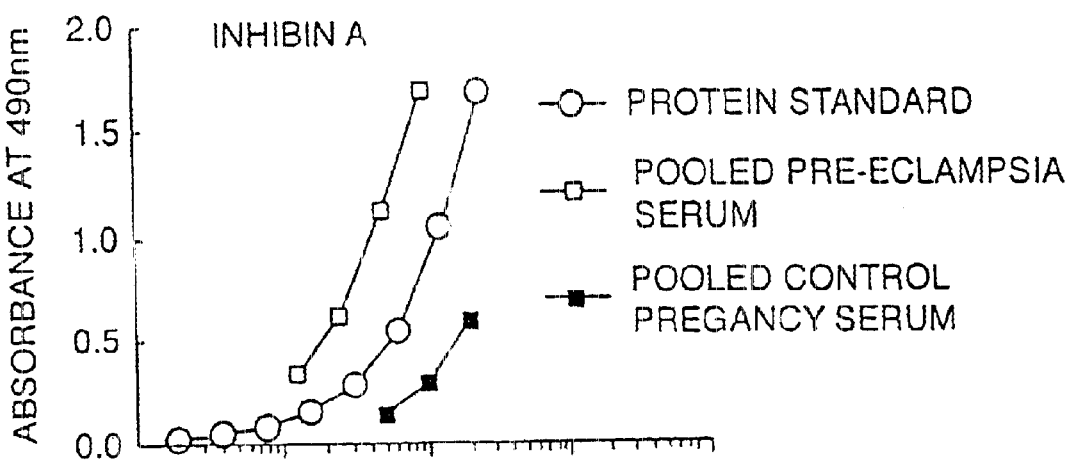
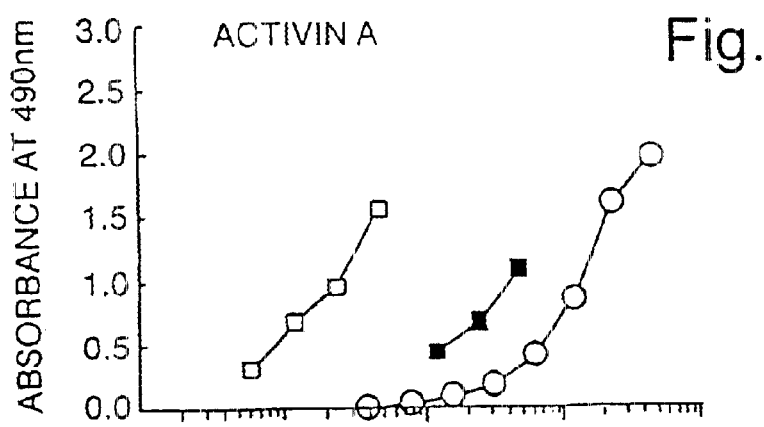
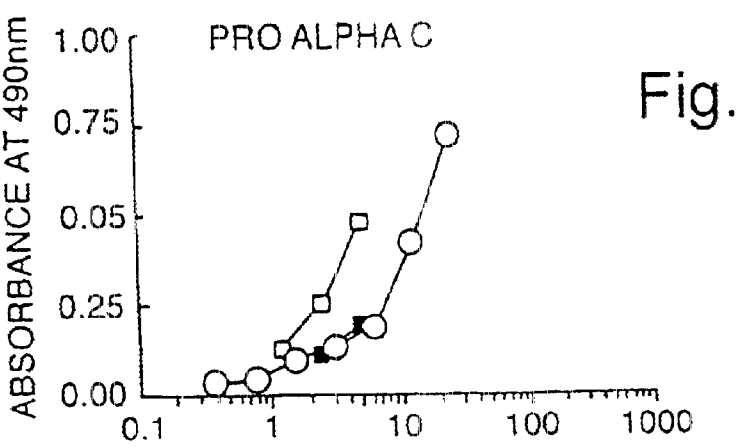

DIAGNOSIS OF PRE-ECLAMPSIA

This is a continuation of application Ser. No. 09/214,599, filed Aug. 30, 1999, now abandoned, which is a 371 application of PCT/GB97/01880, filed Jul. 11, 1997.

This invention relates to detection of pre-eclampsia. In particular, it relates to early diagnosis of pre-eclampsia by detecting elevated levels of the hormone inhibin A.

Pre-eclampsia, otherwise known as gestational proteinuric hypertension (GPH) is a multisystem disease of pregnancy of unknown cause. The maternal syndrome is characterised by various abnormalities: increased blood pressure, oedema, proteinuria and abnormal clotting, liver and renal function. The cause of pre-eclampsia is believed to lie in the placenta and there is evidence for a circulating endothelial cell "toxic" factor which is most likely to originate from the syncytiotrophoblast. The syncytiotrophoblast provides the surface of contact between the placenta and the maternal blood and is a multi-nucleated syncytium with an extensive microvillous brush border.

Pre-eclampsia is a relatively common condition, occuring in approximately one in ten pregnant women. Around 10% of cases will be severe. In severe cases, early delivery may be necessary and there is therefore the risk of the child being handicapped. Pre-eclampsia also remains a danger to the lives of both babies and mothers.

The symptoms of pre-eclampsia described above are generally detectable from around 28 weeks up to full term and are not normally apparent before 24 weeks. The conventional tests are for kidney failure by measuring urea in the blood or protein in the urine, and for increased maternal blood pressure. There are some other indicators of pre-eclampsia, including hormonal ones. However, none of these tests can predict the on-set of pre-eclampsia more than a few days in advance of secondary symptoms becoming fully apparent.

If pre-eclampsia could be detected earlier, before clinical symptoms arise, it would be possible to intervene in affected pregnancies e.g. by treating with anti-hypersensitive drugs, increasing monitoring and foetal surveillance and thereby improve foetal and maternal outcome.

Thus, there is a need for a new test for pre-eclampsia and in particular a test that can predict the on-set of the secondary symptoms of pre-eclampsia earlier than existing tests. Other tests are routinely carried out during pregnancy e.g. spina bifida is tested for at 16 weeks. If pre-eclampsia could be tested for several weeks in advance of the possible onset of symptoms, more time would be available for treatment to avoid the possibility of serious problems arising.

It has now been discovered that the hormone inhibin A is significantly increased in cases of pre-eclampsia compared to normal pregnancies. Before secondary symptoms of pre-eclampsia are detectable, a group of patients who went on to develop pre-eclampsia showed a higher mean inhibin A level than a second group who did not go on to develop pre-eclampsia.

Inhibin A is a member of the family of inhibins which are heterodimeric proteins consisting of $\alpha\beta_A$ (inhibin A) and $\alpha\beta_B$ (inhibin B) subunits. The term "inhibin A" as used herein refers to the dimeric protein, which is the biologically active form of inhibin A. The two protein subunits are joined together by disulphide bonds. Inhibin A is produced mainly by the ovaries and has an endocrine role in inhibiting pituitary follicle stimulating hormone (FSH) production. In pregnancy, circulating levels of inhibin A are increased with the placenta being the major source (Muttukrishna et al 1995). In contrast, inhibin B levels are not elevated in either control or pre-eclampsia pregnancies.

EP 185 034 discloses one dimeric form of inhibin, which it identifies in terms of molecular weight, subunit structure and other properties. The sizes given are 14 kD±2 kD and 44 kD. Later research suggests that the primary active form of inhibin A in biological fluids is a 32 kD molecule formed by a 12 kD $\beta_A$ and 20 kD subunit. The 32 kD inhibin is the mature form produced by post-translational processing of precursor forms of molecular weight 65 kD and 56 kD. Immunoreactive $\alpha$ monomer also circulates in the body. The various different circulating inhibin proteins are often together referred to as "inhibin forms".

It has also been discovered that maternal peripheral serum concentrations of the related hormones pro alpha C and activin A, when measured as total activin A, are significantly elevated in pre-eclampsia compared to normal maternal serum. Activins are homodimers consisting of $\beta_A\beta_A$ (activin A), $\beta_A\beta_B$ (activin AB) and $\beta_B\beta_B$ (activin B) subunits linked by disulphide bridges. Activin A occurs naturally in free form and in bound form, bound to a protein called follistatin. "Total" activin A refers to both activin A whether free or bound. Pro alpha C is a part of the $\alpha$ subunit of inhibin A which is not present in the biologically active dimer. Serum human chorionic gonadotrophin (hCG) concentrations are also significantly higher in pre-eclampsia compared to normal pregnancy serum.

Khalil et al 1995 and Petraglia et al 1995 discuss hormone levels during normal and abnormal pregnancies but do not describe or suggest any possibility of a test for pre-eclampsia.

The present invention provides in one aspect a method of diagnosis of pre-eclampsia which method comprises measuring inhibin A in a biological sample.

Diagnosis according to the invention includes predictive diagnosis of pre-eclampsia, that is a prediction that the secondary symptoms of pre-eclampsia such as high blood pressure will occur.

Preferably, the sample is a maternal body fluid. The sample may be a serum or plasma sample from the maternal blood. Alternatively, it may be for example an amniotic fluid sample.

In another aspect, the invention provides the use of inhibin A levels as an indicator of pre-eclampsia.

The invention may further comprise measuring the level of other proteins, which may be hormones and the use of other such proteins together with inhibin A as indicators of pre-eclampsia. The additional proteins measured may be one or more of the hormones activin A, pro alpha C and hCG. Where activin A is measured, this is preferably total activin A.

The way in which measurement of inhibin A is carried out is not material to the invention. Recently developed specific and sensitive assays for inhibin A are described by Groome et al 1994; and Muttukrishna et al 1994. The presently preferred manner for measuring inhibin A in a biological sample uses one antibody specific for the alpha-subunit of inhibin A and a second antibody specific for the beta-subunit of inhibin A.

In yet another aspect, the invention provides the use of an antibody system specific for inhibin A in a test for pre-eclampsia.

In accordance with the invention, levels of all molecular forms of dimeric inhibin A are preferably measured, irrespective of molecular size. However, the measurement of specifically the mature 32 kD form of the protein may be sufficient for the purposes of the invention.

In accordance with the present invention, it has been demonstrated that inhibin A levels are significantly increased in pre-eclamptic pregnancies over normal pregnancies. Not only that, it has also been found that there is no overlap in inhibin A levels between pre-eclamptic and normal pregnancies. Furthermore, it has been demonstrated that at an early stage in gestation, before the secondary symptoms of pre-eclampsia are normally detectable, a significantly higher inhibin A level is detectable in a group of patients who go on to develop pre-eclampsia compared to a control group of individuals who do not have a pre-eclamptic pregnancy.

A clinically useful screening test for women at risk of pre-eclampsia has not previously existed. Detection of patients at high risk of pre-eclampsia before the disease develops will allow increased surveillance, monitoring of foetal growth and well-being and placental function. It may also lead to new methods of intervention to stabilise blood pressure and renal function and possibly reduce the severity of the disease. Any intervention which can prolong pregnancy safely will reduce the burden of prematurity which remains one of the major causes of foetal mortality and neonatal and childhood handicap.

In the attached figures:

FIG. 1 shows assay validation curves constructed from levels of inhibin A, activin A and pro alpha C in maternal samples from pre-eclamptic and control pregnancies;

Figure 2A:
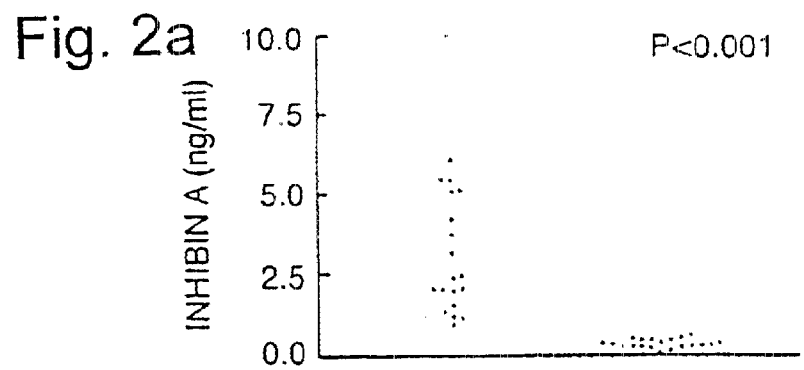
FIG. 2 shows individual concentrations of inhibin A, activin A, pro alpha C and hCG in individual maternal serum samples in pre-eclamptic and control pregnancies.
Figure 2B:
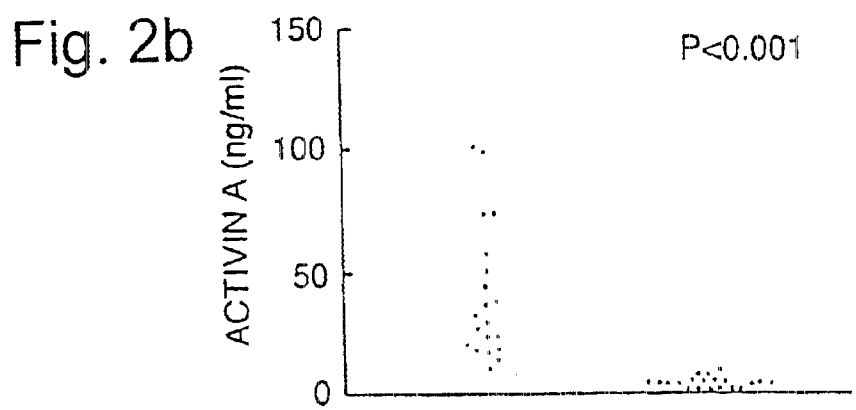
Figure 2C:
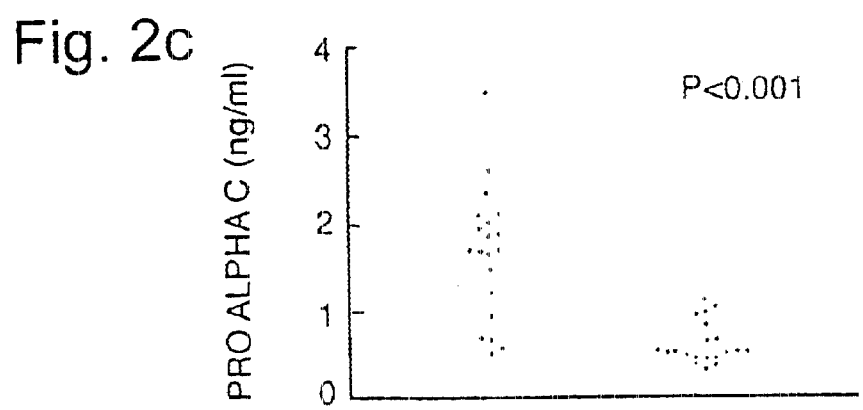

The invention will now be further described in the following examples.

EXAMPLES

Materials and Methods

Sample Collection

Blood samples obtained from 20 pre-eclamptic patients and 20 normal gestational age matched control pregnant women were used for the measurement of the hormones. The samples were obtained at the pre-eclampsia clinic and the antenatal clinic respectively, and had been collected as part of other studies for which patients have given informed consent. Serum was separated by centrifugation and stored at −20° C.

Serum samples collected at 16 weeks gestation for pregnancy screening were analysed. Serum from 15 pregnant women who developed pre-eclampsia later in pregnancy and 54 matched control pregnant women who were normal throughout pregnancy were analysed.

Fractionation of Samples by Chromatography (FPLC)

Serum samples pooled from pre-eclamptic patients (n=20) and control pregnant women (n=20) were fractionated by gel permeation chromatography. 100 µl serum samples were applied to a fast protein liquid chromatography (FPLC) column (Superose 12, Pharmacia Ltd., Milton Keynes, Bucks, UK) which was equilibrated and eluted with phosphate-buffered saline (pH 7.4) containing 0.1% (w/v) polypep (Sigma) and 0.05% (w/v) sodium azide at a flow rate of 0.5 ml/minute. Fractions were collected for the measurement of inhibin A, pro alpha C and activin A. For calibration purposes, the retention times of the following proteins were determined: $\alpha_2$-macroglobulin (750 kDa); alcohol dehydrogenase (150 kDa); bovine serum albumin (66 kDa); recombinant inhibin A (32 kDa); recombinant activin A (24 kDa) and cytochrome C (12.5 kDa).

Hormone Assays

Inhibin A

Serum and FPLC fraction concentrations of dimeric inhibin A were measured in duplicate 5 µl and 25 µl aliquots respectively as described below and elsewhere (Muttukrishna et al, 1994). The mean intra and inter assay variations were 4.3% and 5.1% respectively. Minimum detection limit of the assay for human recombinant inhibin A (kindly provided by Dr. M. Rose, NIBS, UK) was 2 pg/ml.

Inhibin B

Serum concentrations of dimeric inhibin B were measured in duplicate 50 µl using an enzyme immunoassay as described in detail elsewhere (Groome et al, 1996) with some modifications. Minimum detection limit of the assay for human recombinant inhibin B was 30 pg/ml. The mean intra and inter assay variations were 6.2% and 7.2% respectively.

Pro alpha C

Serum and FPLC fraction concentrations of pro alpha C were measured in duplicate 25 µl and 50 µl aliquots respectively as described before (Groome et al, 1995) with some modifications. Minimum detection limit of the assay for pro alpha C standard (Prof. N P Groome) was 5 pg/ml. The mean intra and inter assay variations are 6.8% and 8.6% respectively.

Activin A

Serum and FPLC fraction concentrations of dimeric activin A were measured using an EIA specific for 'total' activin A as described below and elsewhere (Knight et al, 1996). The mean intra and inter assay variations were 6.5% and 7.7% respectively. The minimum detection limit of the assay for human recombinant activin A (Genentech, USA) was 50 pg/ml.

hCG

Serum concentrations of hCG were measured using immulite-chemiluminescent assay kits (Diagnostic Products Ltd.). All samples were assayed in the same assay and the mean intra assay variation was <10%.

Two-site Enzyme Immunoassay for Dimeric Inhibin-A

Coating of Plates with E4 Capture Antibody

Monoclonal antibodies against the $\beta_A$ subunit of human inhibin were covalently linked to 96-well hydrazide plates (UniSyn Technologies Inc., Tustin, Calif., USA) through their carbohydrate moieties. Immediately before use, plates were washed (10 cycles) with enzyme immunoassay wash buffer (0.05% Tween 20 (Sigma, UK) in 0.05 M Tris buffer pH 7.5) on a microplate washer and dried by inversion onto paper towelling.

Preparation and Oxidation of Standards and Samples

Recombinant human inhibin A or purified 32 kDa bovine inhibin used as reference preparations were serially diluted in enzyme immunoassay diluent alone [10% (w/v) bovine serum albumin (BSA), 5% (v/v) mouse serum (Sigma), 5% (v/v) Triton X-100, 0.15 M sodium chloride in 0.1 M Tris-HCl buffer pH 7.5] or in enzyme immunoassay diluent mixed with an equal volume of pooled human post-menopausal serum (PMS). Serum samples were diluted as appropriate in enzyme immunoassay diluent (normally a 1:1 dilution of normal cycle serum: 1:10 dilution of hyperstimulated serum; 1:2000 dilution of human follicular fluid). Dilutions of standards and samples were made in 2.5 ml disposable plastic tubes. Pre-assay oxidation of standards and samples was then carried out by adding freshly prepared hydrogen peroxide solution (10% v/v: Sigma) to give a final concentration of 2% (v/v). Tubes were mixed thoroughly and incubated for 30 min at room temperature before transferring 100 μl aliquots to E4-coated plates.

Enzyme Immunoassay Procedure

Plates were placed in a humidity chamber and incubated at 4° on a rocking platform. After overnight incubation, the plates were washed (10 cycles) before adding to each well 50 μl of alkaline phosphate-conjugated a subunit monoclonal antibody [$R_1$ F(ab); 1:32 000 dilution]. After mixing for 2 hours at room temperature on a microplate shaker, plates were washed extensively (18 cycles) with the final three wash cycles made using wash buffer without Tween 20. Quantification of bound alkaline phosphatase was made using a commercially available enzyme immunoassay amplification kit (Immuno Select ELISA Amplification System, Gibco BRL, Uxbridge, UK) which was used according to the supplier's instructions. To minimize the risk of temperature-dependent variation in signal generation, both incubation steps were performed at ambient temperature. After incubation with "kit substrate solution" (50 μl/well) for one hour on a microplate shaker, 50 μl of "kit amplifier solution" was added to each well. The amplification reaction was stopped before blank wells began to show significant color development by adding 50 μl of 0.3 M sulphuric acid (normally stopped after one hour). Absorbance of 492 nm was read on an enzyme immunoassay plate reader and data processed by immunoassay curve-fitting software (Riacalc. Pharmacia-LKB, Milton Keynes, UK).

Activin A Enzyme Immunoassay

Activin A concentrations were measured using a 2-site EIA. Briefly, standards (recombinant human activin A) and samples were diluted as appropriate in PBS containing 10% (w/v) bovine serum albumin (BSA) and 0.1% (w/v) sodium azide. 125 μl volumes of diluted samples and standards were transferred to 1.5 ml microfuge tubes and mixed with an equal volume (125 μl) of distilled water containing 20% (w/v) sodium dodecyl sulphate (SDS). After a 10 min incubation at 90–95° C. tubes were cooled before adding 20 μl hydrogen peroxide solution (30% v/v; Sigma). After a further 10 min incubation at room temperature, duplicate 100 μl aliquots of denatured and oxidized samples/standards were transferred to E4 antibody-coated microtitre plates containing 25 μl EIA plate buffer/well (0.1M Tris-HCl, 0.15M NaCl, 10% (w/v) BSA, 5% (v/v) Triton X-100 and 0.1% (w/v) sodium azide; pH 7.5). After adding to each well 25 μl EIA plate buffer containing ~35 ng biotinylated E4 monoclonal antibody, plates were incubated overnight in a humidified box at ambient temperature. After washing (15 cycles) with EIA wash buffer (0.05M Tris-HCl, 0.15M NaCl, 0.05% v/v Tween-20, 0.05% v/v sodium azide, pH 7.5), 50 μl alkaline phosphatase-conjugated Extravidin (1:10,000 v/v; Sigma) was added and plates were incubated for 2 hours at room temperature in a humidified box. Plates were washed thoroughly (18 cycles) and bound alkaline phosphatase quantitated using a commercially available ELISA amplification kit (Immunoselect ELISA Amplification system, Gibco-BRL, Uxbridge, UK) according to the supplier's instructions. The limit of detection was 10 pg/well and intra- and inter-assay coefficients of variation (CV) were 5.0 and 9.1% respectively. Cross-reaction of rh inhibin A, inhibin B and activin B were <0.5%. Cross-reaction of rh follistatin-288 (gift from NIDDK) and bovine pro-αC were <0.1%. Neither follistatin (500 ng/ml) or human α2 macroglobulin (α2M; 100 μg/ml; Calbiochem) interfered in the assay and recovery of activin A standard added to human serum samples was 96±5% (n=12 samples).

Statistical Analysis

Unpaired student's t-tests were carried out to compare the concentrations of hormones of control and pre-eclamptic patients. Spearman correlation analyses were carried out to investigate the relationship between hormones, platelet counts and blood pressure in pre-eclampsia. All statistical analysis were carried out using Graph Pad Prism statistical package using 95% confidence interval limit.

Results

A) For Serum Samples Taken between 20 and 38 Weeks Gestation (Mean 29 Weeks)

Behaviour of Normal and Pre-eclamptic Pregnancy Sera in the EIAs

Serial dilutions of control and pre-eclamptic serum gave response curves in the inhibin A (FIG. 1a), pro alpha C (FIG. 1c) and activin A (FIG. 1b) enzyme immunoassays which were parallel to that for the human recombinant inhibin A standard, human pro alpha C standard and human inhibin B standard respectively. Recovery of exogenous human recombinant inhibin A (3.8 pg/well), human recombinant activin A (100 pg/well) and pro alpha C (5 pg/well) added before assay to aliquots of control pregnancy serum (105±6%, 113±13%, 98±3.2% respectively) and pre-eclampsia serum (94.9±6.7%, 122.4±19.2%, 105±10.5% respectively) were almost quantitative.

Serum Concentration of Inhibin A, Pro Alpha C and Activin A (FIG. 2)

Maternal serum concentrations of inhibin A (FIG. 2a) were increased by ~8 fold (P<0.001) in pre-eclampsia compared to control pregnancies. Peripheral concentrations of pro alpha C (FIG. 2c) were almost 3 fold (P<0.001) enhanced and levels of activin A (FIG. 2b) were significantly (~9 fold, P<0.001) elevated in pre-eclampsia.

Serum Concentrations of hCG

Figure 2D:
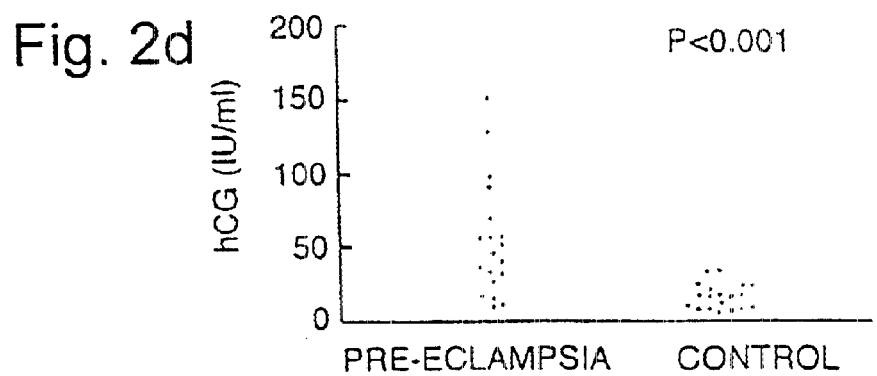

Peripheral serum concentration of hCG was ~4 fold higher (P<0.001) in pre-eclampsia (59.05±9.27 IU/ml)) compared to control pregnancy (16.3±1.84 IU/ml)) maternal serum (FIG. 2d).

Figure 3A:
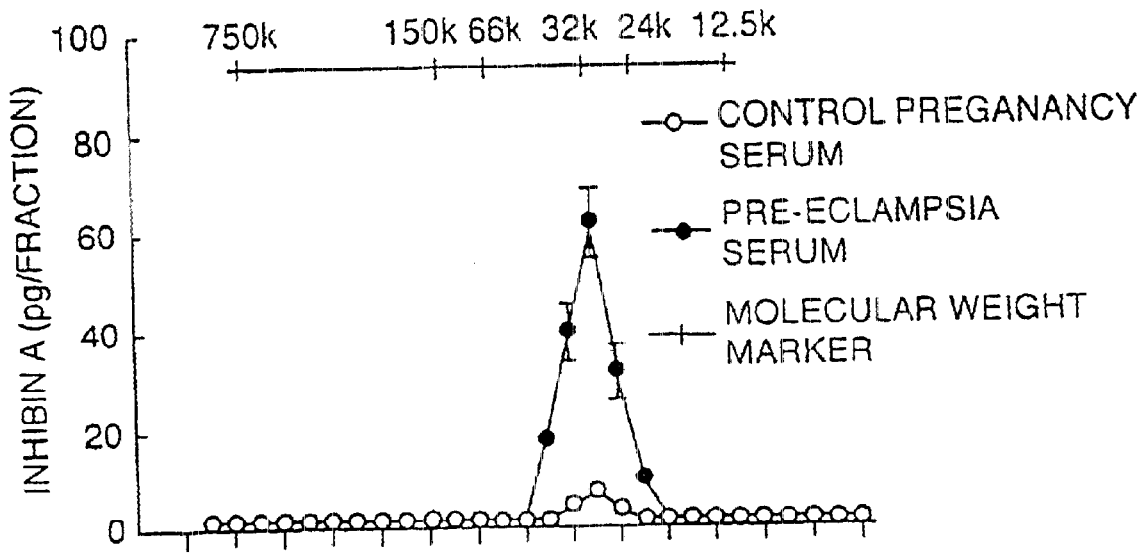
FIG. 3 shows a profile of inhibin A and activin A immunoreactivity after FPLC gel-permeation chromatography of control and pre-eclampsia maternal serum.
Figure 3B:
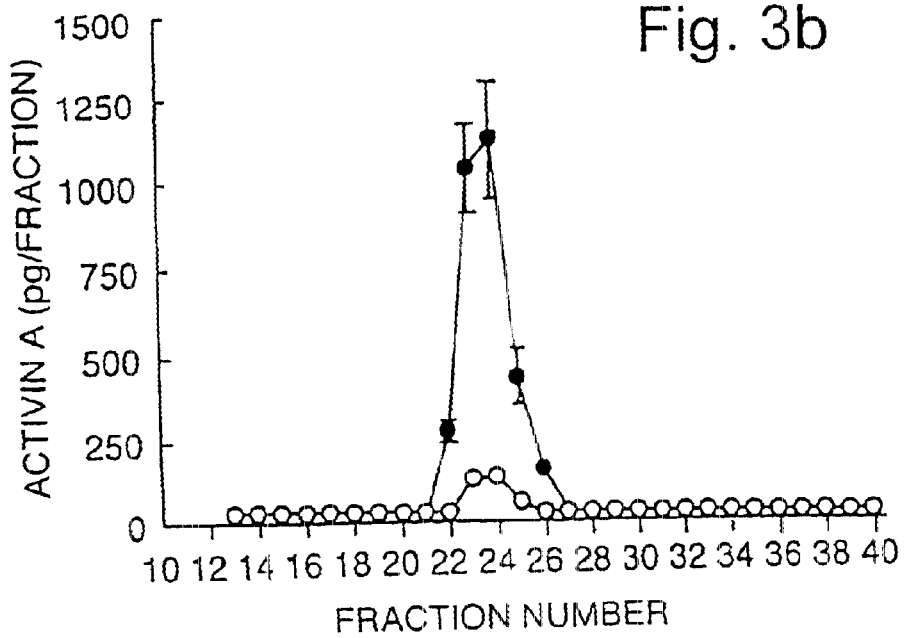
Figure 4:
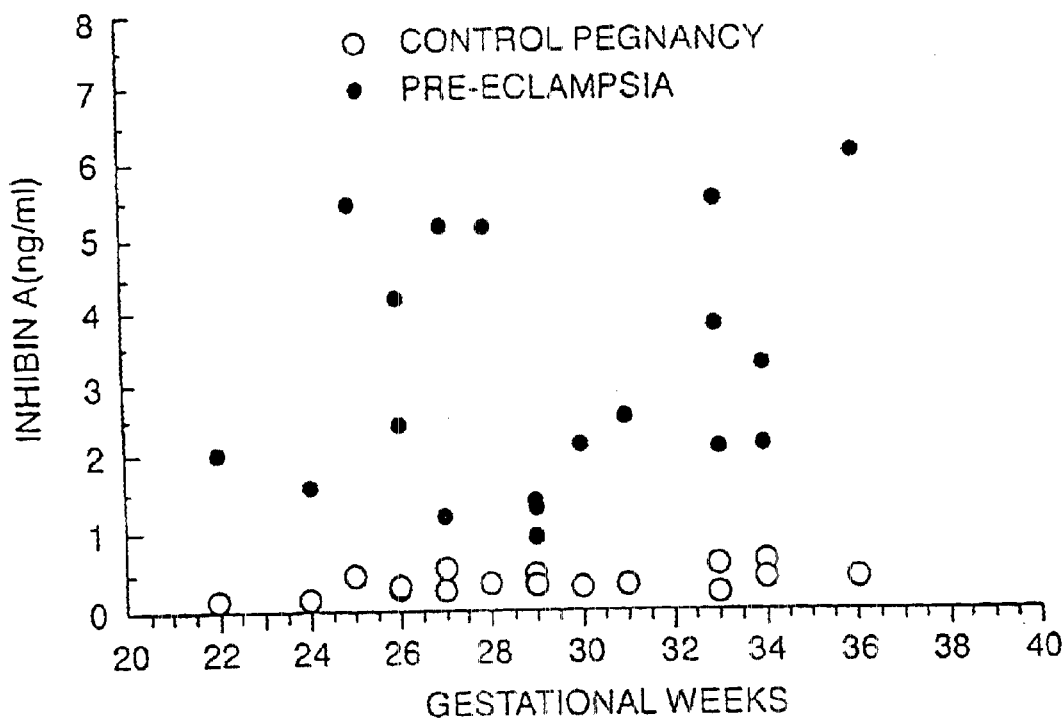
FIG. 4 shows maternal serum inhibin A concentrations in normal and pre-eclamptic pregnancies at different stages of pregnancy. Numerical values are given in Table 1.

Gel Permeation Chromatography (FIG. 3)

Measurement of inhibin A and activin A in the chromatographic profiles of pooled pre-eclamptic and control pregnancy sera detects only one major peak of inhibin A (32 kDa) and activin A (>100 kDa) in the enzyme immunoassays. Levels of pro alpha C were just above the detection limit in the pre-eclamptic serum fractions and undetectable in the control serum chromatographic fractions. Inhibin A co-eluted with the human recombinant inhibin A(32 kDa) and represents the fully processed mature form of inhibin A. However, activin A immunoreactivity eluted with an apparent molecular weight >100 kDa suggesting that almost all activin A in circulation is bound to activin binding proteins with no detectable 'free' activin A corresponding to the elution position of human recombinant activin A (~25 kDa).

B) For Serum Samples at 16 Weeks Gestation

Figure 5:
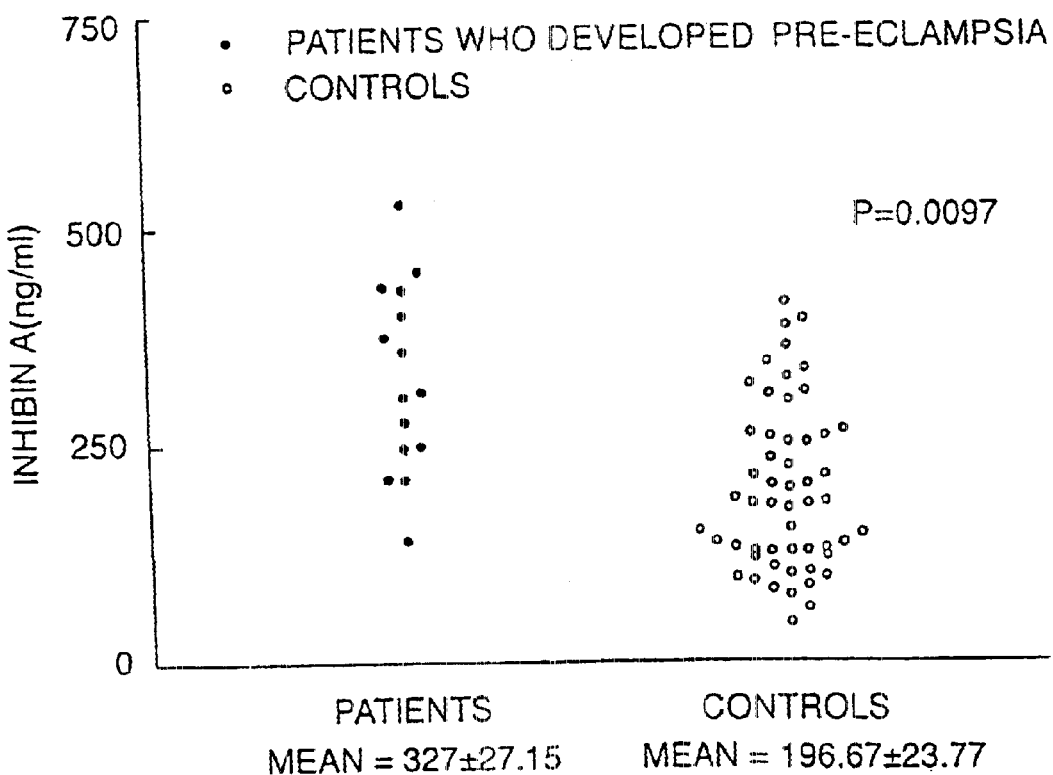
FIG. 5 shows maternal serum inhibin A concentrations in individuals at 16 weeks gestation, for a group of patients who go on to develop pre-eclampsia and for a second group who do not develop pre-eclampsia.

Measurement of serum inhibin A in samples taken at 16 weeks gestation indicates a significantly higher mean inhibin A concentration for a group of individuals who went on to suffer pre-eclampsia (327±27.15 pg/ml), compared to a control group who did not develop pre-eclampsia (197.67±23.77 pg/ml) (P=0.0097). Results are shown in FIG. 5.

REFERENCES

Groome, N. P., Illingworth P. J., O'Brien, M., Cooke, I., Ganesan, T. S., Baird, D. T. and McNeilly, A. S., (1994) Clinical Endocrinology, 40, 717–723.

Groome, N. P., Illingworth, P. J., O'Brien, M., Priddle, J., Weaver, K. and McNeilly, A. S. (1995) Journal of Clinical Endocrinology and Metabolism, 80, 2926–2932.

Groome, N. P., Illingworth, P. J., O'Brien, M., Pai, R, Rodger, F. E., Mather, J., and McNeilly, A. S. (1996) Journal of Clinical Endocrinology and Metabolism (in press).

Khalil, A., Kaufmann, R. C., Wortsman, J., Winters, S. J. and Huffmann, D. G. (1995) Am.J.Obstet. Gynaecol. 172, 1019–1025.

Knight, P. G., Muttukrishna S., and Groome N. P. (1996) Journal of Endocrinology 148, 267–279.

Muttukrishna, S., Fowler, P. A., Groome, N. P., Mitchell, G. G., Robertson, W. R. and Knight, P. G., (1994) Human Reproduction 9, 1634–1642.

Muttukrishna, S., George, L., Fowler, P. A., Groome, N. P., and Knight, P. G., (1995) Clinical Endocrinology 42, 391–397.

Petraglia, F., Aguzzoli, L., Gallinelli, A., Florio, P., Zonca, M., Benedetto, C., and Woodruff, K. (1995) Placenta 16, 447–454.

Figure Legends

FIG. 1 Parallel response curves for serial dilutions of protein standard, pooled control pregnancy serum and pooled pre-eclampsia serum in the (a) inhibin A, (b) activin A and (c) pro alpha C enzyme immunoassays. Values are means of duplicate determinations of absorbance.

FIG. 2 Scatter plot of individual concentrations of a) inhibin A, b) activin A, c) pro alpha C and d) hCG in maternal serum in pre-eclampsia (n=20) and control pregnancy (n=20).

FIG. 3 Profile of (a) inhibin A and (b) activin A immunoreactivity measured by EIA after FPLC gel-permeation chromatography of 100 µl samples of control or pre-eclampsia maternal serum. Values are mean ±SEM (n=3 separate fractionations). The elution positions of the following proteins are indicated: $\alpha_2$-macroglobulin (Vo; 725 kDa), alcohol dehydrogenase (AD; 150 kDa) bovine serum albumin (BSA; 66 kDa), recombinant human inhibin A (32 kDa), human recombinant activin A (24 kDa) and cytochrome C (12.5 kDa).

Hormone Concentrations in Maternal Serum

TABLE 1

| Gestational age (days) | Gestation (weeks) | parity | inhibin A (ng/ml) | activin A (ng/ml) | Pro alpha C (ng/ml) | hCG (IU/ml) |
|---|---|---|---|---|---|---|
| PRE-ECLAMPSIA | | | | | | |
| 206 | 29 | 0 + 0 | 1.26 | 10.97 | 0.67 | 33.79 |
| 187 | 27 | 0 + 0 | >10 | 74.52 | 2.02 | 152.08 |
| 217 | 31 | 0 + 0 | 2.50 | 44.94 | 1.24 | 58.64 |
| 198 | 28 | 0 + 0 | 5.12 | 75.20 | 0.53 | 10.37 |
| 206 | 29 | 0 + 0 | 1.40 | 24.35 | 1.72 | 70.92 |
| 184 | 26 | 0 + 0 | 2.40 | >100 | 0.57 | 57.34 |
| 229 | 33 | 0 + 0 | 2.07 | 19.38 | 1.50 | 35.26 |
| 191 | 27 | 0 + 0 | 5.15 | 51.43 | 0.71 | 27.85 |
| 173 | 25 | 0 + 0 | 5.45 | 39.10 | 1.70 | 98.71 |
| 233 | 33 | 0 + 0 | 5.48 | 33.30 | 0.96 | 47.82 |
| | | Mean | 3.43 | 41.47 | 1.16 | 59.28 |
| | | SEM | 0.61 | 7.57 | 0.18 | 13.63 |
| 165 | 24 | 1 + 1 | 1.58 | 17.55 | 2.14 | 18.38 |
| 205 | 29 | 0 + 0 | 0.93 | 30.04 | 1.90 | 129.17 |
| 249 | 36 | 1 + 0 | 6.08 | 20.68 | 3.50 | 91.49 |
| 191 | 27 | 0 + 0 | 1.17 | 14.73 | 1.96 | 56.87 |
| 212 | 30 | 0 + 0 | 2.12 | 101.98 | 1.88 | 12.22 |
| 153 | 22 | 1 + 0 | 2.01 | 18.58 | 1.76 | 52.55 |
| 239 | 34 | 0 + 0 | 2.10 | 27.93 | 2.39 | 131.56 |
| 183 | 26 | 1 + 3 | 4.19 | 37.37 | 2.64 | 16.56 |
| 228 | 33 | 2 + 0 | 3.76 | 57.80 | 1.69 | 40.76 |
| 236 | 34 | 0 + 1 | 3.22 | 23.64 | 2.11 | 38.68 |
| | | Mean | 2.72 | 35.03 | 2.20 | 58.82 |
| | | SEM | 0.50 | 8.44 | 0.17 | 14.01 |
| | | Mean(n = 20) | 3.05 | 38.08 | 1.68 | 59.05 |
| | | SEM | 0.38 | 5.46 | 0.17 | 9.28 |
| CONTROL | | | | | | |
| 213 | 30 | 0 + 0 | 0.37 | 7.22 | 0.47 | 33.23 |
| 198 | 28 | 0 + 0 | 0.54 | 3.49 | 0.49 | 23.25 |
| 208 | 30 | 0 + 0 | 0.31 | 4.37 | 0.44 | 18.06 |
| 193 | 28 | 0 + 0 | 0.34 | 4.39 | 0.53 | 16.79 |
| 210 | 30 | 0 + 0 | 0.47 | 5.23 | 1.05 | 18.38 |
| 191 | 27 | 0 + 0 | 0.26 | 3.51 | 0.36 | 15.37 |
| 230 | 33 | 0 + 0 | 0.54 | 3.59 | 0.83 | 33.48 |
| 196 | 28 | 0 + 0 | 0.29 | 1.53 | 0.39 | 20.24 |
| 181 | 26 | 0 + 0 | 0.47 | 1.74 | 0.31 | 5.57 |
| 225 | 32 | 0 + 0 | 0.53 | 7.36 | 0.98 | 7.44 |
| | | Mean | 0.41 | 4.24 | 0.58 | 19.18 |
| | | SEM | 0.03 | 0.62 | 0.08 | 2.91 |
| 159 | 23 | 2 + 0 | 0.13 | 1.47 | | 11.80 |
| 205 | 29 | 0 + 0 | 0.29 | 1.95 | 0.52 | 23.36 |
| 250 | 36 | 1 + 0 | 0.39 | 4.56 | 0.94 | 7.83 |
| 197 | 28 | 0 + 0 | 0.25 | 1.38 | 0.55 | 17.06 |
| 223 | 32 | 0 + 0 | 0.28 | 9.85 | 0.64 | 8.37 |
| 142 | 20 | 1 + 0 | 0.11 | 1.71 | | 16.72 |
| 244 | 35 | 0 + 0 | 0.63 | 3.76 | 1.12 | 23.16 |

TABLE 1-continued

| Gestational age (days) | Gestation (weeks) | parity | inhibin A (ng/ml) | activin A (ng/ml) | Pro alpha C (ng/ml) | hCG (IU/ml) |
|---|---|---|---|---|---|---|
| 194 | 28 | 2 + 0 | 0.32 | 3.64 | 0.67 | 9.27 |
| 216 | 31 | 1 + 0 | 0.21 | 4.05 | | 6.38 |
| 223 | 32 | 0 + 0 | 0.41 | 4.19 | 0.53 | 10.19 |
| | | Mean | 0.30 | 3.66 | 0.71 | 13.41 |
| | | SEM | 0.05 | 0.79 | 0.07 | 1.98 |
| | | Mean(n = 20) | 0.36 | 3.95 | 0.63 | 16.30 |
| | | SEM | 0.03 | 0.49 | 0.06 | 1.84 |

What is claimed is:

1. A method of diagnosis of pre-eclampsia, which method comprises measuring the level of inhibin A in a biological sample taken from a pregnant woman and comparing said level to a normal reference value, whereby elevation of inhibin A above normal is indicative of pre-eclampsia.

2. The method as claimed in claim 1, wherein the biological sample is from maternal blood.

3. The method as claimed in claim 1, wherein the level of inhibin A is measured by means of an immunoassay.

4. The method as claimed in claim 1, wherein the method further comprises the additional measurement of the level of at least one additional protein chosen from the group consisting of activin A, pro alpha C and hCG.

* * * * *